United States Patent
Chammas

(10) Patent No.: US 11,738,288 B2
(45) Date of Patent: Aug. 29, 2023

(54) AUTOMATED SYSTEM AND METHOD TO ISOLATE SPECIFIC CELLS FROM BLOOD OR BONE MARROW

(71) Applicant: Jacques Chammas, Walpole, MA (US)

(72) Inventor: Jacques Chammas, Walpole, MA (US)

( * ) Notice: Subject to any disclaimer, the term of this patent is extended or adjusted under 35 U.S.C. 154(b) by 433 days.

(21) Appl. No.: 16/915,401

(22) Filed: Jun. 29, 2020

(65) Prior Publication Data

US 2021/0402328 A1 Dec. 30, 2021

(51) Int. Cl.
*B01D 17/12* (2006.01)
*B01D 21/26* (2006.01)
*B01L 3/00* (2006.01)
*G01N 33/49* (2006.01)

(52) U.S. Cl.
CPC .......... *B01D 17/12* (2013.01); *B01D 21/262* (2013.01); *B01L 3/50215* (2013.01); *G01N 33/491* (2013.01); *B01L 2200/026* (2013.01); *B01L 2300/0861* (2013.01); *B01L 2400/0409* (2013.01); *B01L 2400/0478* (2013.01); *B01L 2400/0605* (2013.01)

(58) Field of Classification Search
CPC .. B01D 17/12; B01D 21/262; B01D 2221/10; B01D 17/0217; B01L 3/50215; B01L 2200/026; B01L 2300/0861; B01L 2400/0409; B01L 2400/0478; B01L 2400/0605; B01L 2300/0803; B01L 2300/0864; B01L 2400/0633; B01L 3/502753; G01N 33/491; B04B 2005/045; B04B 5/0428; B04B 5/0442; B04B 13/00
See application file for complete search history.

(56) References Cited

U.S. PATENT DOCUMENTS

| | | |
|---|---|---|
| 5,489,386 A | 2/1996 | Saunders |
| 5,641,628 A | 6/1997 | Bianchi |
| 5,714,325 A | 2/1998 | Bianchi |
| 5,840,502 A | 11/1998 | Van Vlasselaer |
| 6,123,655 A | 9/2000 | Fell |
| 6,210,889 B1 | 4/2001 | Drouin et al. |
| 7,316,932 B2 | 1/2008 | Woodside |
| 8,435,785 B2 | 5/2013 | Slukvin et al. |
| 8,585,971 B2 | 11/2013 | Huang et al. |
| 8,747,289 B2 | 6/2014 | Coelho |
| 8,774,488 B2 | 7/2014 | Parikh et al. |
| 8,876,683 B2 * | 11/2014 | Chammas ........... A61M 1/0209 |
| 9,217,131 B2 | 12/2015 | Lamish et al. |
| 9,217,697 B2 | 12/2015 | U'Ren et al. |
| 9,334,477 B2 | 5/2016 | Takamura et al. |
| 9,381,293 B2 | 7/2016 | Eberle |
| 10,081,014 B2 | 9/2018 | Toner et al. |

(Continued)

*Primary Examiner* — Waqaas Ali

(57) ABSTRACT

The present invention provides an automated system and method to isolate nucleated blood cells from whole blood or bone marrow. A disc mounted to a centrifuge system with spinning rotor is used to manipulate cells by channeling fluids while subjected to high gravitational field. The disc embodies at least two axisymmetric processing stations connected by a circular channel. Each station contains multiple chambers connected by fluidic channels to controllably transfer fluids. First stage separation allows for the isolation of the buffy coat layer while the second stage separation utilizes gradient density fluids to isolate the targeted nucleated cells from the buffy coat layer in the spinning disc.

20 Claims, 11 Drawing Sheets

(56) References Cited

U.S. PATENT DOCUMENTS

| | | |
|---|---|---|
| 10,518,275 B2 | 12/2019 | Sengun et al. |
| 2008/0087613 A1* | 4/2008 | Hudock .............. A61M 1/3696 210/782 |
| 2014/0323284 A1* | 10/2014 | Chammas ............. B04B 5/0428 494/7 |

* cited by examiner

AUTOMATED SYSTEM AND METHOD TO ISOLATE SPECIFIC CELLS FROM BLOOD OR BONE MARROW

BACKGROUND OF THE INVENTION

New therapeutic applications in the modern medicine rely on different types of human cells to treat a variety of diseases and conditions. Regenerative cells are used to restore damaged tissues or organs in the body and to re-establish their normal function. It is estimated that one in three Americans could potentially benefit from regenerative medicine. Hematopoietic progenitor cells (HPCs) collected from bone marrow or from umbilical blood, are used in the treatment of many malignant (leukemia, lymphoma) and non-malignant (sickle cell disease) diseases to replace or rebuild a patient's hematopoietic system. Immune cells and Hematopoietic Stem Cell Therapy (HSCT) are used for the treatment of Multiple sclerosis (MS) autoimmune disease. T-cells are essential for human immunity for their ability to scan, identify, hunt, and kill cancerous cells or germ infected cells. Advanced methods of re-engineering T-cells are being developed for cancer treatment. Iliac cells isolated from bone marrow are used for spine fusion surgeries.

Nucleated red blood cell (NRBC) that can be isolated from maternal blood to establish fetus DNA and chromosome information. Fetal gene diagnosis at an early stage of pregnancy can be safely achieved without any risk to the fetus or to the mother.

All these cells mentioned above, are isolated by processing collected human blood or extracted bone marrow. The quality of the cells is dependent on the processing method and on the technical and the environmental logistics. Establishing a reliable and a simple method and a system to repeatedly and consistently isolate the targeted cells from collected blood samples; is a crucial and vital need.

The present invention provides a simple and a reliable automated system and method that isolates specifically targeted cells from whole blood or bone marrow. Particularly to isolate immune cell, regenerative cells, and T-cells from blood; and to isolate an enriched colony of fetal nucleated red blood cell (NRBC) from maternal blood. A fluidic disc mounted to a spinning rotor is used to manipulate cells by channeling fluids while subjected to centrifugal forces. This new system and method allow hospitals and point of care centers to isolate immune cells and T-cells from blood for patient treatment and to isolate fetal NRBC from maternal blood for fetal gene diagnosis at an early stage of pregnancy without any risk of miscarriage or any risk to the fetus or to the mother.

SUMMARY OF THE INVENTION

The present invention provides a new automated system and method that isolates specific cells from whole blood or bone marrow. The system comprises of a fluidic disc, automated centrifuge apparatus, and software. The fluidic disc is mounted to the centrifuge spinning rotor and it is used to manipulate cells by channeling fluids while subjected to centrifugal force. This new system and method allow hospitals and point of care centers to isolate immune cells and T-cells from blood for patient treatment and to isolate fetal NRBC from maternal blood for fetal gene diagnosis at an early stage of pregnancy without a risk of miscarriage.

The system is completely automated and controlled by a software. An operator collects a blood sample (or bone marrow) from a human subject by a standard venipuncture (biopsy for bone marrow) procedure, then transfer the blood into a fluidic disc that can be mounted on a specific centrifuge apparatus. The system processes the blood automatically and stops when a concentrated pool of the desired cells is harvested inside a special chamber on the disc. The disc can be removed from the centrifuge and the pool of the targeted cells can be retrieved.

The centrifuge apparatus having a computer mounted to the rotor and spins with it that is communicating back and forth with a second computer located on the stationary field by 2-way wireless communication scheme. The two computers are managed by the same software and jointly direct all the operations on the centrifuge apparatus.

The rotor is equipped with computer controlled valves, sensors, compressors, pneumatic actuators, motors, pistons, solenoids, and actuators activities. The rotor is equipped with computer controlled drivers to control all valves, sensors, compressors, pneumatic actuators, motors, pistons, solenoids, and actuators activities. The software directs the blood processing operations and manages all modules, devices, and sensors on the centrifuge to execute all tasks of a specified protocol to produce the required results.

The centrifuge rotor is adapted to receive a fluidic disc in a unique setting and interface with it completely. All valve actuators, pump actuators, compressors, pneumatic actuators, and sensors located on the rotor are engaged with matching features on the fluidic disc. In a way for example when a valve actuator is activated a specified fluid path is blocked or opened. Similarly, when pump actuator is activated a fluid is driven from one chamber to another inside the fluidic disc.

The fluidic disc is a one-time use disposable that embodies at least two symmetric (with respect to the axis of rotation) processing stations connected by a peripheral outer channel to ensure a dynamic balance. Each station contains multiple chambers connected by fluidic channels that are controlled by valves, pumps and sensors.

Spring loaded clamps can be used as valves on the disc to occlude the fluid path between different chambers or cavities. These spring loaded clamp valves can be controllably opened by activating actuators such as pneumatic or hydraulic pistons, solenoids, magnetic forces, centrifugal forces, electric motors, pneumatic motors, and the like. All these actuators are controlled by a spinning on the rotor computer and a stationary computer that communicate back and forth with each other and are jointly managed by software. Sensors controlled by the spinning computer and the stationary computer are used to monitor and to report the status of all actuators. Sensors also monitor and report the status of all processed fluids within the disc.

Each station has a separation chamber (also called radially extended chamber) that extends radially toward the center of the disc that coincides with the rotor's center of rotation. All the separation chambers are connected on the outer edge by a peripheral channel.

At the start of the process, when the blood is transferred to the disc, the two separation chambers and the peripheral channel are filled with the blood. The latter distributes the blood evenly between the separation chambers and secures the dynamic balance of the disc. The rotor spins at rotational speed enough to separate the blood components according to their densities. The RBC (non-nucleated) having highest density are disposed radially outward and occupy most of the peripheral channel. The plasma with the lowest density is amassed inside the separation chambers in the sections closest to the axis of rotation. A thin buffy coat layer is formed between the RBC and the plasma layers. The buffy coat contains platelets, leukocytes (Monocytes, Neutrophils, Eosinophils, Basophils, and Lymphocytes). In case maternal blood is used in filling the disc, the fetal NRBCs that have the same size of the lymphocytes and lower density than the standard RBC are mixed in the buffy coat layer.

When separation is accomplished between RBC, plasma, and the buffy coat inside the disc; compressing means start squeezing the peripheral channel slowly while the rotor is spinning. A valve controlling the fluid flow between the separation chamber and the plasma chamber for each processing station is opened. Plasma starts to transfer out of the separation chamber and move into the plasma chamber. The valve controlling the fluid flow between the separation chamber and a secondary chamber that could contain density gradient fluid, remain closed. The concentrated RBC start to migrate from the channel and move evenly toward the separation chambers while forcing the plasma out (the channel continues to balance the fluid between the two separation chambers). Compressors start to slowly squeeze the separation chambers evenly while the rotor is spinning. The plasma is pushed out of each separation chamber into the corresponding plasma chamber located on the same processing station.

Sensors monitor the fluids inside the separation chambers and particularly the fluid inside the stem tube that extend from the separation chamber radially inward. The squeezing effect of the separation chamber stops instantly once certain optic sensor (most likely positioned on the stem tube section) detects the separation line between the plasma and the buffy coat.

The advantage of the long stem tube positioned at the exit port of each separation chamber is to be able to monitor the exact spot of the separation line between different layers. A small inner diameter and relatively long stem tube allows for high precision determination of the exact position of the separation lines between layers of different densities as they are exiting the separation chamber. This allows for accurate decision in determining the start and the end of the exiting flow of each separate layer. This also allows for accurate control in driving each layer exiting the separation chamber to be directed exclusively into its separate chamber without being contaminated with other components from different layers.

In a preferred embodiment each processing station on the disc is equipped with a diaphragm recirculating pump that is used to drive plasma from the plasma chamber back into the separation chamber. The purpose of this plasma flow is to generate a counter current with drag forces acting in the opposite direction of the centrifugal forces. The recirculating plasma that is pumped back into the separation chamber would be forced by the centrifugal force to exit the separation chamber through the stem tube back into the plasma chamber. Consequently, each cell inside the separation chamber that is exposed to the plasma recirculating flow (Specifically the cells that are located in the vicinity of the exit port of the separation chamber and the stem tube) would have two opponent forces acting upon it. First, the centrifugal force which is a function of the rotational speed and cell density is acting on the cell radially in the outer direction. Second, the drag force that is a function of flow speed and the cell size (more specifically the projected surface area of the cell) is acting on the cell radially in the inner direction. The high density cells are pushed radially outward while the large cells are pushed radially inward. The balance between the centrifugal forces and the drag forces help in sorting the cells according to their size and density. In case of pregnant maternal blood separation, the plasma recirculation technique ensures the presence of the maximum number of the NRBC in the buffy coat layer. Furthermore, it ensures the sorting of the NRBC colony in the buffy coat layer. The NRBC cells are most likely mixed with the lymphocytes and the granulocytes. In another embodiment, compressing means can be used to squeeze the plasma chamber to start a plasma recirculating flow back into the separation chamber.

At the end of the plasma recirculation phase, the valve controlling the fluid flow between the separation chamber and the plasma chamber for each processing station is closed. The valve controlling the fluid flow between the separation chamber and a secondary chamber that could contain density gradient fluid, is opened. The compressors resume the pressing action on the separation chambers to slowly drive the concentrated RBC to exit the separation chambers and to crawl into the stem tube. This slow and precise movement of the concentrated RBC inside the stem tube forces the buffy coat layer to flow out of the stem tube and into the secondary chamber that could contain density gradient fluid.

In another embodiment, the plasma chamber valve is opened and the secondary chamber valve is closed for a period of time enough to allow a small segment of the buffy coat that is the closest to the axis of rotation to flow into the plasma chamber. This segment of the buffy coat contains mostly platelets because the platelets are the less dens components in the buffy coat and are generally positioned closer to the axis of rotation.

In another embodiment, the pressing action on the separation chambers to slowly drive the concentrated RBC to exit the separation chambers and to crawl into the stem tube in order to push the buffy coat layer into the secondary chamber, can take place once the blood components are separated inside the rotating disc and directly after pushing the plasma into the plasma chamber. The plasma recirculating action between the plasma chamber and the separation chamber does not need to take place.

The secondary chamber is used to receive the buffy coat layer in whole or in portions of it. This chamber could be used to perform secondary separations in order to isolate desired cell colonies from the buffy coat layer.

In a preferred embodiment, the secondary chamber has two sections separated by a flexible gorge. An interior section that is located radially inward with respect to the gorge, and an exterior cavity that is located radially outward with respect to the gorge. A valve can be used at the gorge to prevent any fluid communication between the interior section and the exterior cavity. The disc can be supplied with empty secondary chamber or with a secondary chamber having density gradient fluid.

In another embodiment the density gradient fluid inside the secondary chamber could be mixed with hypertonic or hypotonic fluid that could alter its osmotic pressure. For example, the density gradient fluid can be mixed with solution to bring its osmotic pressure at a range of 100 mOsm to 700 mOsm. Or a range of 300 mOsm to 600 mOsm. Or a range of 400 mOsm to 550 mOsm. The density of the blood cells can be increased or decreased by exposing the cells to hypertonic or hypotonic medium.

In another embodiment, the hypertonic or the hypotonic solution could be separate from the gradient density solution but it has a lower density. The gradient density fluid remain in the radially outward section of the secondary chamber while the hypertonic or the hypotonic fluid remains in the radially inward section of the secondary chamber.

In another embodiment the disc is equipped with a third or an intermediate chamber positioned between the end of the stem tube and the secondary chamber that may or may not contain density gradient fluid. This third chamber contains hypertonic or the hypotonic solution that could alter the density of blood cells.

When the transfer of the buffy coat layer, to the gradient density chamber is completed, the valve controlling fluid flow to the secondary chamber is closed.

Generally, the buffy coat layer could contain platelets, monocytes, lymphocytes, and granulocytes. In case pregnant maternal blood is used, the buffy coat layer could contain platelets, monocytes, lymphocytes, granulocytes, and the fetal NRBC cells.

In another embodiment a portion of the buffy coat that is the closest to the axis of rotation is transferred to the plasma chamber. The buffy coat portion that is transferred to the secondary chamber that contains gradient density fluid, could contain monocytes, lymphocytes, and granulocytes.

In another embodiment where the monocytes and the lymphocytes are targeted, and the granulocytes are not desired. The buffy coat portion that contains monocytes, lymphocytes, and granulocytes is transferred to the secondary chamber that contains gradient density fluid. It is preferred that the gradient density fluid has a density lighter than the granulocytes density but higher than the lymphocytes density. It is also preferred that the gradient fluid chamber that is also defined as the third chamber has a special geometry in the radially outer section. The radially outward end of the chamber is split in two wells. One well "first well" extends radially outward and receives most of the density gradient fluid along with all the cells that have a density higher than the density gradient fluid. A valve controls the entrance to the second well.

The first well is filled with the density gradient fluid and all the high density cells are trapped at the bottom of the well. Consequently, the valve controlling the entrance to the second well is opened and the gradient fluid along with the less dense lymphocytes and the monocytes are rushed into the second well. Then the valve is closed. The second well is equipped with ports to drain or to recover all its contents by a syringe or a pipette. In another embodiment the second well forms a chamber that can be detached from the disc while all the harvested lymphocytes are trapped inside it.

In another embodiment, if the granulocytes are targeted, then the density of the density gradient fluid has to be lower than the density of the granulocytes and higher than the density of the lymphocytes. The granulocytes will precipitate in a cavity that is located radially outward with respect to the gorge. A valve can be used at the gorge to trap the granulocytes inside the chamber. The cavity is equipped with ports to drain or to recover all its contents by a syringe or a pipette.

In another embodiment where the fetal NRBC cells are targeted. The buffy coat layer (platelets, monocytes, lymphocytes, granulocytes, and the fetal NRBC cells) is transferred to the gradient density chamber. The secondary chamber inside the fluidic disc contains specialty medium that is prepared by mixing density gradient solution with NaCl solution to bring its osmotic pressure to a level that can increase the density of the NRBC to a level higher than the gradient solution.

In another embodiment, the density of a medium used can be adapted such as having two chunks of density fluids having different densities riding on the top of each other. For example, having Percoll solution with density 1.085 g/ml riding on Percoll solution with density 1.095 g/ml. The valve controlling the flow into the gradient density chamber is closed. The rotor speed gradually drops to the vicinity of 100 rpm (or it stops) for a period of time enough to allow for the NRBC to increase its density. This osmotic pressure and exposure time are enough for the fetal NRBC cells to have their density higher than the density of the gradient solution. The leukocytes are slow to respond to the hypertonic solution during this duration and their density wouldn't change. If the exposure time to the hypertonic solution is increased the density of the leukocyte would increase. Therefore, the exposure timing must be closely monitored.

The rotor increases its rotational velocity to regain the centrifugal forces that ensures blood components separation. Only the cells with a density higher than the gradient fluid density along with the fetal NRBC, precipitate at the bottom of the exterior cavity. This exterior cavity is located radially outward with respect to the gorge of the density gradient chamber. The gorge occlusion valve is activated to prevent any fluid movement between the interior section and the exterior cavity of the third chamber (gradient density chamber).

The cavity is equipped with ports to drain or to recover all its contents by a syringe or a pipette. In a preferred embodiment, the disc encompasses a detachable chamber positioned radially outward with respect to the exterior cavity.

This detachable chamber is designed to receive the NRBC from the exterior cavity by centrifugal forces once a valve that controls the fluid flow between the cavity and the NRBC detachable chamber is opened.

The rotor spins at about 100 rpm for a period of time enough to ensure the complete transfer of the NRBC to the detachable chamber. Then the valve is closed and the centrifuge is stopped.

In another embodiment, a sensor (could be optic sensor) is positioned on the channel connecting the exterior cavity and the detachable NRBC chamber to determine the completion of the fluid transfer process between the cavity and the enriched NRBC chambers. Then the valve is closed and the centrifuge is stopped.

The fluidic disc is removed from the rotor and the detachable NRBC chamber is disconnected from the disc. The fluid inside detachable NRBC chamber is drained out. Staining such as May-Grünwald-Giemsa is used to stain the nucleated cells and to identify the fetal NRBC cells under the microscope.

The NRBC fetal cells are detected and separated from the harvested colony of the nucleated cells. DNA analysis such as Polymerase Chain Reaction (PCR) are conducted on the isolated NRBC to determine fetus DNA and chromosome information.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

FIG. 7B—A schematic view demonstrating the secondary chamber containing a mixture of a hypertonic or hypotonic solution and a gradient density fluid.

FIG. 8B—A schematic view demonstrating a third chamber containing hypertonic or hypotonic solution and a second chamber containing gradient density fluid.

FIG. 9B—A schematic view demonstrating the harvesting of lighter cells (monocytes & lymphocytes) in the secondary chamber with two wells.

DETAILED DESCRIPTION OF THE INVENTION

Figure 1:
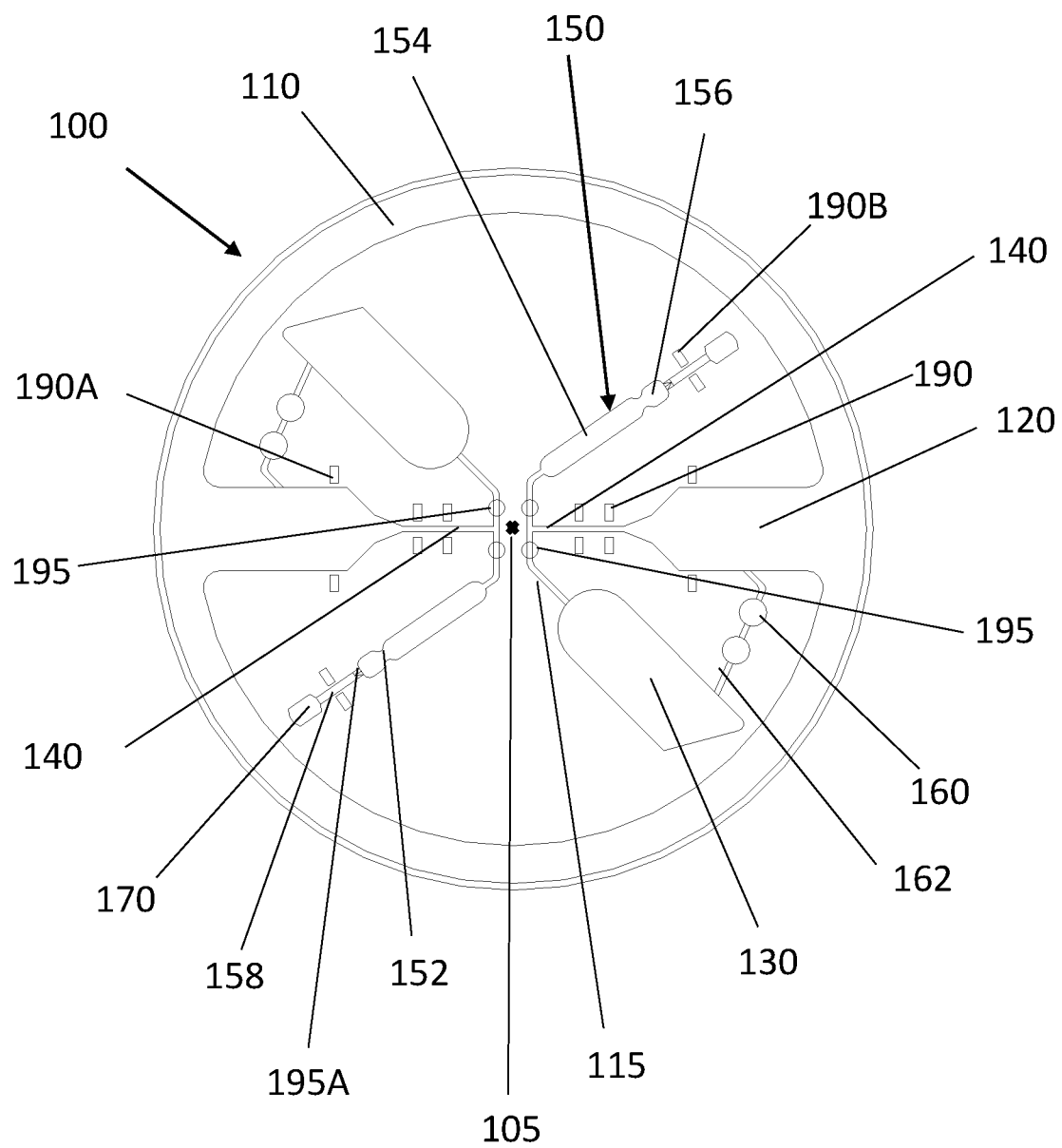
FIG. 1—A schematic view of the fluidic disc and the interface with valves and sensors on the centrifuge rotor.

Referring to FIG. 1 a schematic view of the fluidic disc 100 and the interface with valves and sensors on the centrifuge rotor. Two axisymmetric processing stations connected by a peripheral outer channel 110 are shown on the disc. Each station contains multiple chambers connected by fluidic channels 115 that are controlled by valves, pumps and sensors. The outer channel is used as a reservoir for the processed blood, and it maintains the dynamic balance of the spinning disc by fluidly connecting the two processing chambers. The disc and the centrifuge rotor rotate about the axis of rotation 105 that is perpendicular to the surface of the disc and passes through its center. This axis of rotation is identical for the disc and for the centrifuge rotor.

As shown in FIG. 1, each processing station comprises a separation chamber 120 that extends radially from the outer channel 110 toward the axis of rotation. The interior end of the separation chamber is tapered down to merge into a stem tube 140. The stem tube is preferred to be long enough to be engaged with multiple sensors 190. It is also preferred to be transparent to accommodate optic sensors and light sensors. The elongated stem tube having a small inner diameter to increase the accuracy in detecting the different components of the fluid that passes through.

The end of the stem tube is connected fluidic channels that splits into two directions. One fluidic channel 115 connects the end of the stem tube to the plasma chamber 130. While another fluidic channel 117 connects the end of the stem tube to a secondary chamber also known as the gradient density fluid chamber 150. The plasma chamber 130 extends radially outward inside the disc but it stops short of the outer channel 110. The deep end of the plasma chamber has a well 132 to trap any platelets or cells that are transferred to the plasma chamber.

A back channel 162 connects the plasma chamber 130 to the separation chamber 120. This channel is used only to recirculate the plasma from the plasma chamber back into the separation chamber via a diaphragm pump 160. The diaphragm pump assembly do not allow any flow in the opposite direction. The diaphragms used in the pumping mechanism are integrated into the fluidic disc assembly, while all the pistons and the synchronized valves associated with the pumping mechanism are integrated on the centrifuge rotor. Pneumatic pistons or electrical solenoids are used to activate the pumping mechanism. In a preferred embodiment, a series of spring loaded pistons activated by a rotating cam action are used to drive the pumping mechanism.

Fluidic channel 117 connects the end of the stem tube to the gradient density fluid chamber 150. This chamber contains gradient density fluid 300. The gradient density fluid could be mixed with hypotonic or hypertonic solution 310 that alters the osmotic pressure of the fluid to controllably manipulate the density of the floated or suspended cells in the fluid. The gradient density chamber comprises two cavities that are connected by a flexible gorge 152. The larger cavity that is located radially inward (closer to the axis of rotation 105) with respect to the gorge is called the interior chamber 154. The smaller cavity that is located radially outward with respect to the gorge is called the exterior cavity 156. The flexible gorge can be closed by an actuator on the rotor to prevent fluid flow between the interior chamber 154 and the exterior cavity 156. A fluidic channel 158 extends radially and connects the outer edge of the exterior cavity to a detachable chamber 170. A valve 195A or a breakable seal control the flow of the fluid through the channel 158. A sensor 190B detects the density of the blood components and other fluids in the flow stream.

In another embodiment, the fluidic channels 158 of each processing station are all set to converge to one common chamber that preferably located in the central part of the disc.

The fluidic disc is equipped with special ports (not shown in the figure) that are used to supply the blood to the disc for processing. The ports can be accessed by a syringe with a lure or a needle. The ports can have a screw cover. It is preferred to have two ports or more that are axis-symmetrically positioned on the disc and equidistantly separated in order to preserve the dynamic balance of the spinning disc.

Figure 2:
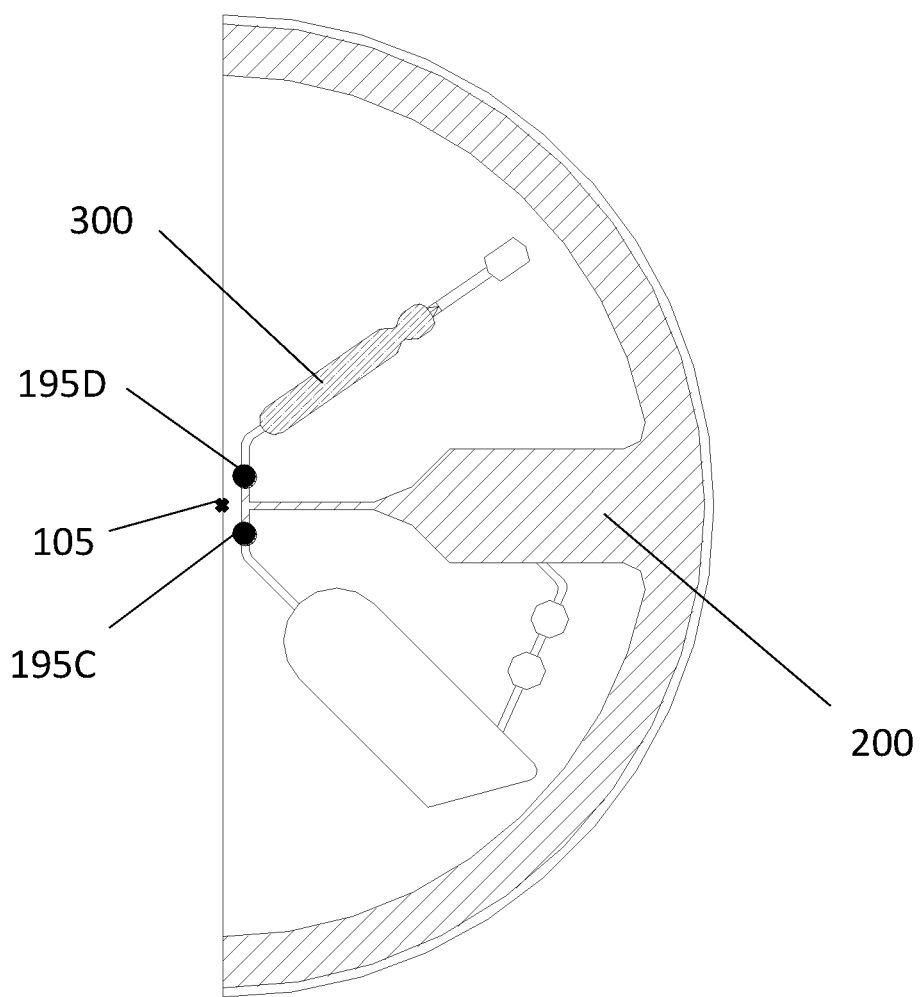
FIG. 2—A schematic view of a portion of the disc encompassing one processing station filled with blood prior processing FIG. 3—A schematic view of a portion of the disc encompassing one processing station demonstrating blood components separation layers.

Referring to FIG. 2, at the start of the process, the blood is transferred to the disc through one of the special ports. When the disc is at rest, the two separation chambers 120 and the peripheral channel 110 are filled with the blood 200. The valve 195C that controls fluid flow to the Plasma chamber 130 is closed. Similarly, the valve 195D that controls fluid flow to the gradient density fluid chamber 150 is closed. The gradient density fluid chamber contains gradient density fluid 300. The rotor spins at rotational speed enough to separate the blood components according to their densities.

Figure 3:
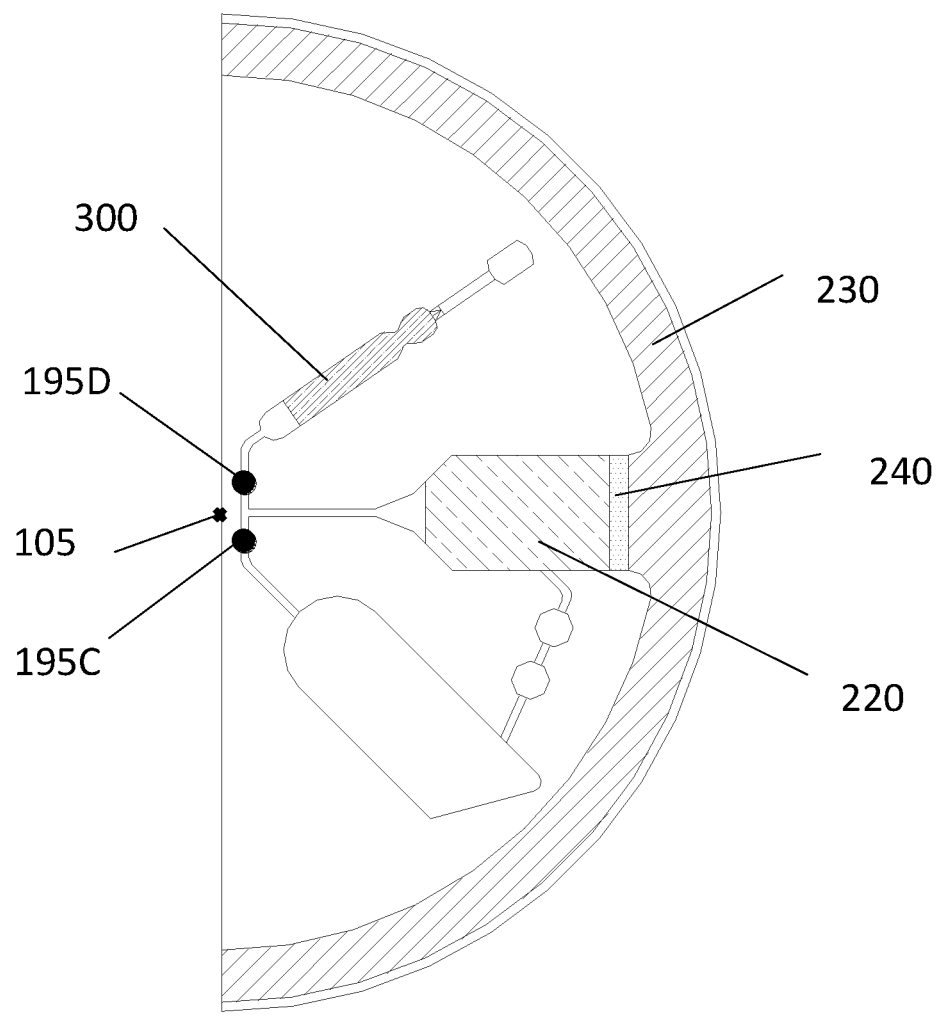

Referring to FIG. 3, the RBC 200 (non-nucleated) having highest density are disposed radially outward and occupy most of the peripheral channel. The plasma 220 with the lowest density is amassed inside the separation chambers in the sections closest to the axis of rotation. A thin buffy coat 240 layer is formed between the RBC and the plasma layers. The buffy coat contains platelets, leukocytes (Monocytes, Neutrophils, Eosinophils, Basophils, and Lymphocytes). In case maternal blood is used in filling the disc, the fetal NBRC cells are mixed in the buffy coat layer. The gradient density fluid 300 remains in its chamber. Valves 195C and 195D remain closed.

When separation is accomplished between RBC, plasma, and the buffy coat inside the disc; compressing means (not shown) start squeezing the peripheral channel slowly while the rotor is spinning. These compression means comprise inflatable pouches that share a confined space inside the disc with the peripheral channel. When the pouches are inflated by a pneumatic or hydraulic pressure they compress the fluid out of the channel. In other embodiment, the peripheral channel has at least one flexible wall that could be pressed by plates activated by pneumatic or hydraulic inflatable pouches or bellows. These plates could by also be activated by different actuators such as motors, pistons, or solenoids to press on the peripheral channel flexible walls.

Figure 4:
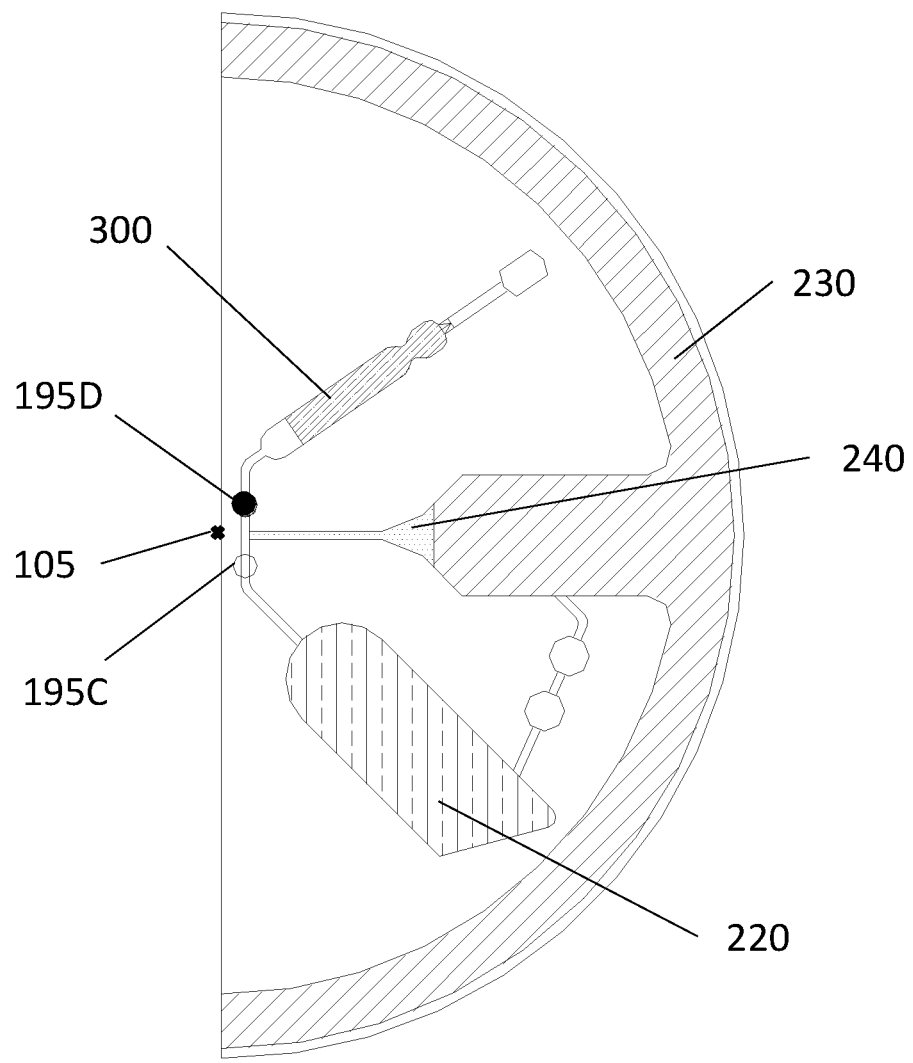
FIG. 4—A schematic view of a portion of the disc encompassing one processing station demonstrating the transfer of the plasma layer.

Referring to FIG. 4, valve 195C controlling the fluid flow between the separation chamber and the plasma chamber for each processing station is opened. Valve 195D controlling the fluid flow between the separation chamber and a secondary chamber that could contain density gradient fluid, remain closed.

As the compressing means slowly squeezes concentrated RBC 230 out of the peripheral channel 110, and force it to migrate toward the separation chambers 120 (the channel continues to maintain the fluid balance between the two separation chambers); the plasma 220 is transferred out of the separation chamber into the plasma chamber 130. Compression means start to slowly squeeze the separation chambers evenly and the plasma is pushed out of each separation chamber into the corresponding plasma chamber located on the same processing station. Compression means used to squeeze the separation chambers are similar to the one used to squeeze the peripheral channel. Optic sensors 190 monitor the fluids inside the separation chambers and particularly the fluid inside the stem tube 140 that extends radially inward from the separation chamber toward the axis of rotation 105. The squeezing effect of the separation chamber stops instantly once an optic sensor positioned on the stem tube detects the separation line between the plasma and the buffy coat 240.

Figure 5:
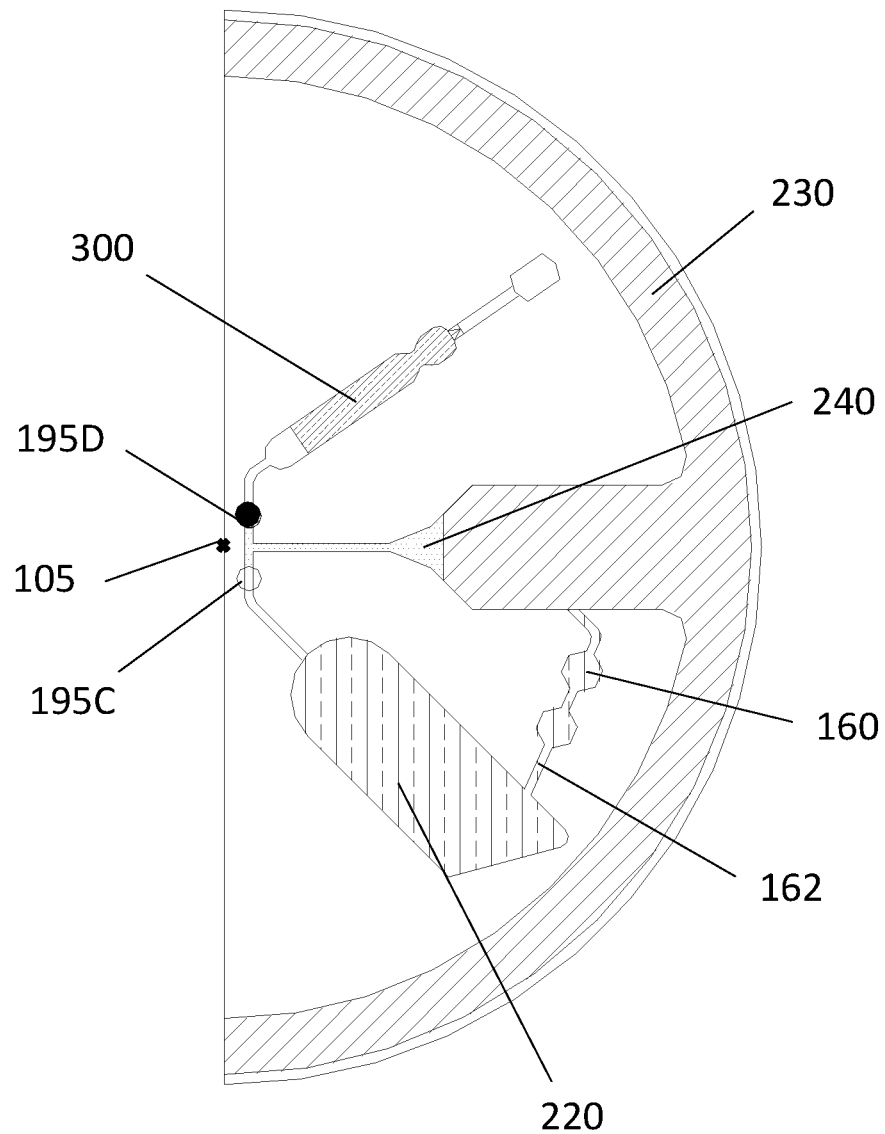
FIG. 5—A schematic view of a portion of the disc encompassing one processing station demonstrating recirculating plasma pumping.

Referring to FIG. 5, a back channel 162 connects the plasma chamber 130 to the separation chamber 120. This channel is used only to recirculate the plasma from the plasma chamber back into the separation chamber via a diaphragm pump 160.

The purpose of this plasma flow is to generate a counter current with drag forces acting in the opposite direction of the centrifugal forces. The recirculating plasma that is pumped back into the separation chamber would be forced by the centrifugal force to exit the separation chamber through the stem tube back to the plasma chamber. Consequently, each cell inside the separation chamber that is exposed to the plasma recirculating flow would have two opponent forces acting upon it.

First, the centrifugal force which is a function of the rotational speed and cell density is acting on the cell radially in the outer direction. Second, the drag force that is a function of recirculating plasma flow speed and the projected surface area of the cell; is acting on the cell radially in the inner direction. The high density cells are pushed radially outward while the large cells are pushed radially inward. The balance between the centrifugal forces and the drag forces help in sorting the cells according to their size and density. For example a nucleated red blood cell (NRBC) has the same size as the spherical lymphocytes with a density (1.075-1.085) g/ml is pushed radially inward; while the standard red blood cell (RBC) is smaller in size (7 µm diameter disc shape) with density 1.1 g/ml is pushed radially outward.

The plasma flow further helps in driving the NRBC out of the RBC bed inside the separation chamber to be mixed with the buffy coat layer that has cells of the same size and density. The plasma recirculation operation can last for 10 minutes, 20 minutes, or up to 60 minutes at different pumping speeds and rotor speeds to attain the proper segregation of all types of cells. This technique can help in sorting all the cells in the buffy coat layer for the platelets, mononuclear leukocytes (monocytes and lymphocytes), and granulocytes leukocytes (basophils, neutrophils, and eosinophils). In case of pregnant maternal blood separation, the plasma recirculation technique ensures the presence of the maximum number of the NRBC in the buffy coat layer. Furthermore, it ensures the sorting of the NRBC colony in the buffy coat layer.

The extended length of the stem tube at the exit port help in aligning the different leukocytes and NRBC cells inside the buffy coat with respect to size and density. Whereas platelets, monocytes, and lymphocytes are positioned inside the stem tube closer to the axis of rotation. While the granulocytes and the NRBC are positioned inside the stem tube closer to the exit port of the separation chamber. The NBRC cells are most likely mixed with the lymphocytes and the granulocytes.

Figure 6:
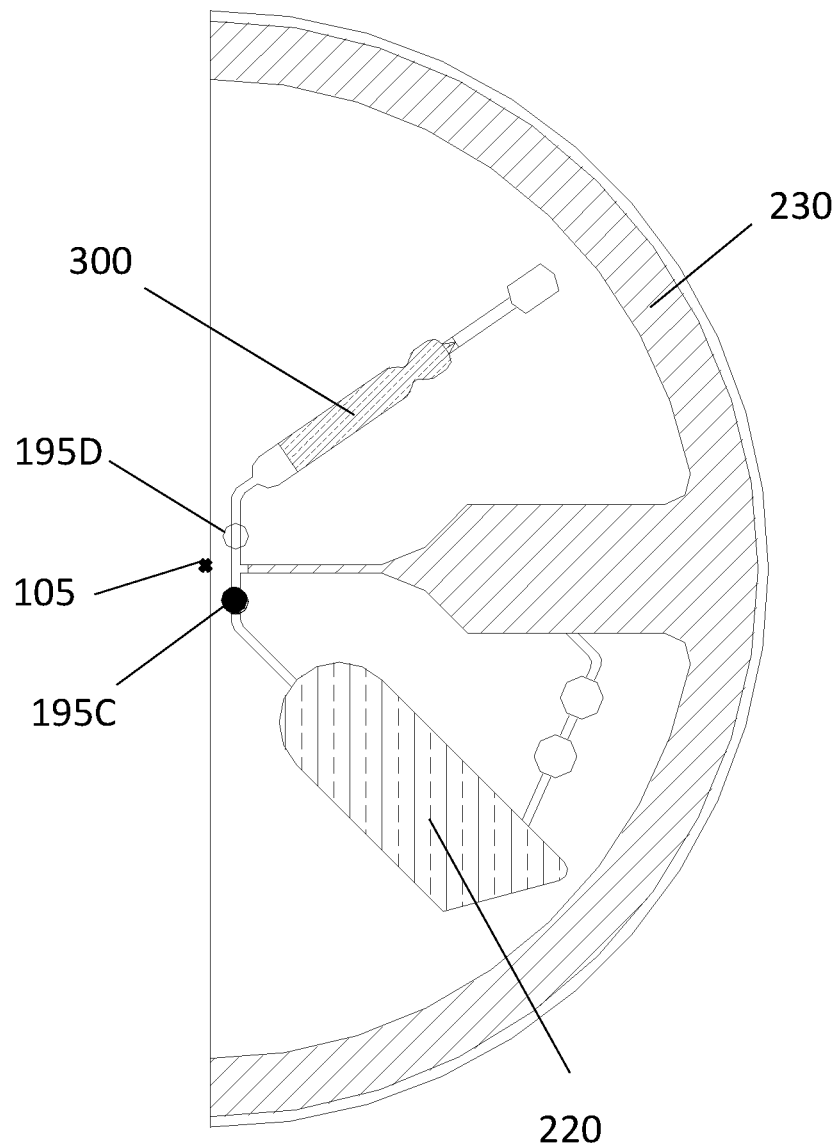
FIG. 6—A schematic view of a portion of the disc encompassing one processing station demonstrating the transfer of the buffy coat layer.

At the end of the plasma recirculation phase, the valve 195C is closed and the valve 195D is opened as shown in FIG. 6. The compressing means resume the pressing action on the separation chambers to slowly and precisely force the buffy coat layer to flow out of the stem tube and into the secondary chamber that could contain density gradient fluid.

The extended length of the stem tube and its small inner diameter allow for the buffy coat layer to move at very low speed. The buffy coat is pushed radially inward by the squeezing effect on the concentrated red cell inside the separation chamber, while it is subjected to a centrifugal force that push the buffy coat radially outward. When the squeezing effect is increased enough to generate a pressure force inside the stem tube higher than the centrifugal force, the buffy coat layer moves radially forward in the exiting direction (toward the axis of rotation). Inversely, when the squeezing effect is decreased to generate pressure force inside the stem tube less than the centrifugal force, the buffy coat layer retreats backward to the separation chamber. By controllably increasing or decreasing the squeezing effect on the separation chamber, the buffy coat layer can selectively move forward or backward inside the stem tube. Optic sensors monitoring the flow inside the stem tube and are capable of distinguishing between different layers of blood components. These sensors can precisely detect the interface between plasma and buffy coat and the interface between buffy coat and RBC layer. With the precise movement of the buffy coat layer coupled with the precise detection of the interface between the buffy coat and the RBC layer; the system can transfer pure buffy coat inside the secondary chamber without RBC contamination.

In the embodiment where the whole buffy coat layer is targeted as a product to be harvested, the secondary chamber is empty and contains no fluid. The buffy coat is transferred to the secondary chamber until the optic sensors on the stem tube detect the red cell layer 230. The compressing action stops and the valve 195D is closed. Therefore, the system can be used for applications that require to harvest pure bone marrow without RBC contamination, to harvest pure stem cells without RBC contamination, to harvest iliac cells without RBC contamination, and to harvest leukocytes without RBC contamination.

In another embodiment where only the platelets are targeted as a product to be harvested, the secondary chamber is empty and contains no fluid. Valve 195C is closed and valve 195D is opened for a period of time enough to allow a small segment of the buffy coat that is the closest to the axis of rotation to flow into the secondary chamber. This segment of buffy coat the contains mostly platelets because the platelets are the less dens components in the buffy coat and are generally positioned closer to the axis of rotation 105. Therefore, the system can be used for applications that require to harvest platelets.

In another embodiment where only the nucleated cells are targeted as a product to be harvested, valve 195C is opened and the secondary chamber valve 195D is closed for a period of time enough to allow a small segment of the buffy coat that rich with platelets and is the closest to the axis of rotation to flow into the plasma chamber. Then, valve 195C is closed and valve 195D is opened to allow for the remained portion of the buffy coat to flow into the secondary chamber. Compression action continues until the optic sensors on the stem tube detect the red cell layer 230. The compressing action stops and the valve 195D is closed.

Figure 7A:
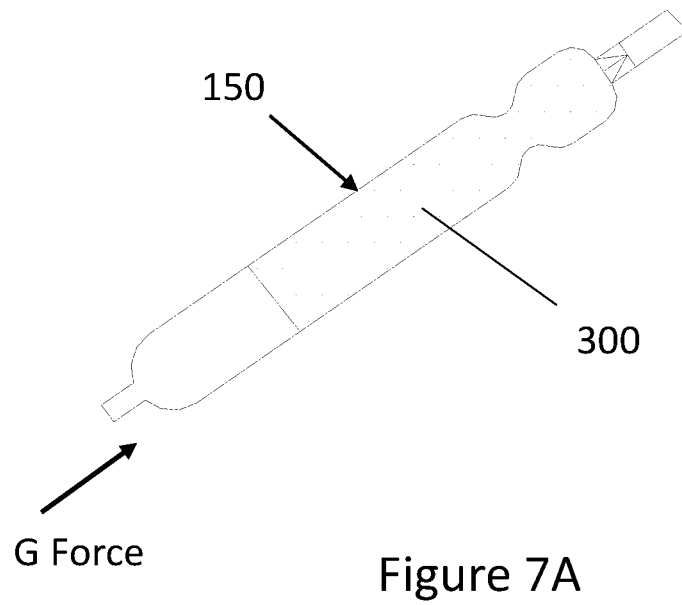
FIG. 7A—A schematic view demonstrating the secondary chamber containing gradient density fluid.

FIG. 7A depict density gradient fluid 300 inside the secondary chamber 150. Density gradient fluids are selected from a group consisting of but not restricted to Percoll solution, Ficoll solution, Polymorphprep solution, sucrose, Nycodenz, and OPTIPrep.

Figure 7B:
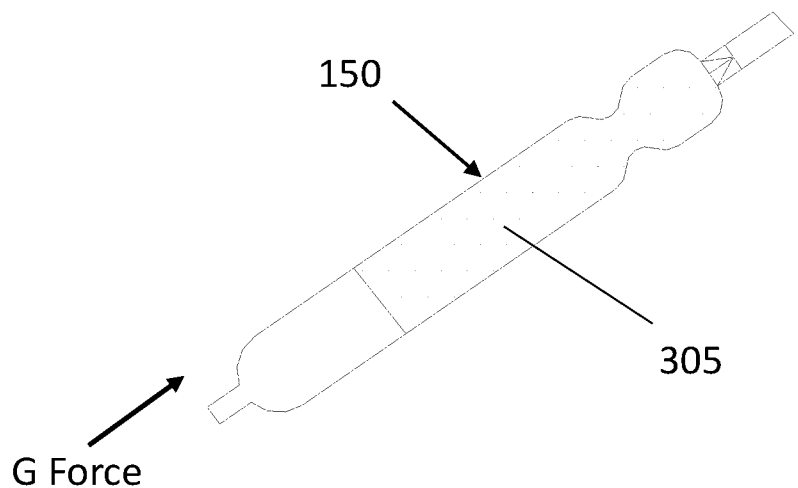

In another embodiment FIG. 7B, a mixture 305 is obtained by adding hypertonic or hypotonic fluid 310 to the density gradient fluid 300 to alter its osmotic pressure. Hypertonic solution having osmotic pressure higher than the saline, could draw water out of the blood cells therefore, increasing its density. Contrary, hypotonic solution having osmotic pressure less than the saline, could pump water into of the blood cells therefore, decreasing its density.

For example, the density gradient fluid can be mixed with solution to bring its osmotic pressure at any value of a range of 100 mOsm to 700 mOsm. Or a range of 300 mOsm to 600 mOsm. Or a range of 380 mOsm to 450 mOsm. The density of the blood cells can be increased or decreased by exposing the cells to hypertonic or hypotonic medium.

Figure 8A:
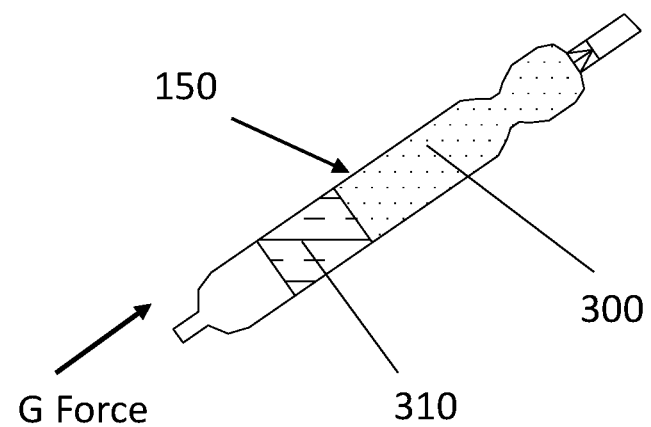
FIG. 8A—A schematic view demonstrating the secondary chamber containing a layer of less dens hypertonic or hypotonic solution on the top of a more dens gradient density fluid.

In another embodiment FIG. 8A, the hypertonic or the hypotonic solution 310 could be separate from the gradient density solution 300 but it has a lower density. The gradient density fluid remain in the radially outward section of the secondary chamber while the hypertonic or the hypotonic fluid remains in the radially inward section of the secondary chamber. In this configuration the cells with lower density remain suspended in the hypertonic or the hypotonic fluid while the heavier cells are mixed in the density gradient fluid.

Figure 8B:
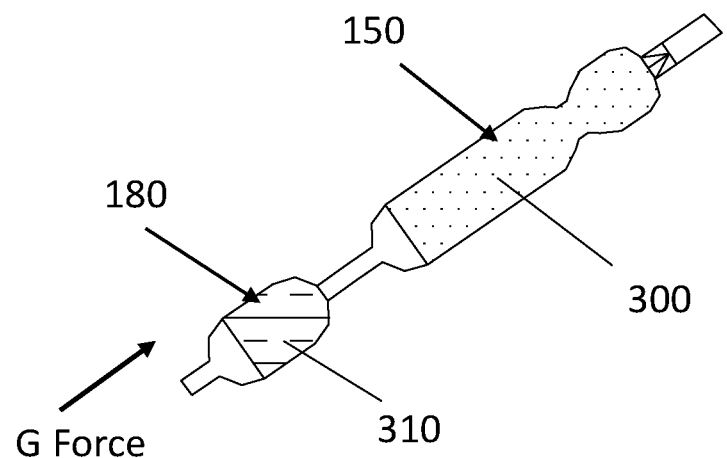

In another embodiment FIG. 8B, the disc is equipped with a third or an intermediate chamber 180 positioned between the end of the stem tube and the secondary chamber 150 that may or may not contain density gradient fluid. This third chamber contains hypertonic or the hypotonic solution 310 that could alter the density of blood cells.

In another embodiment where the buffy coat portion that is transferred to the secondary chamber compose mainly of monocytes 260, lymphocytes 270, and granulocytes 280.

Figure 9A:
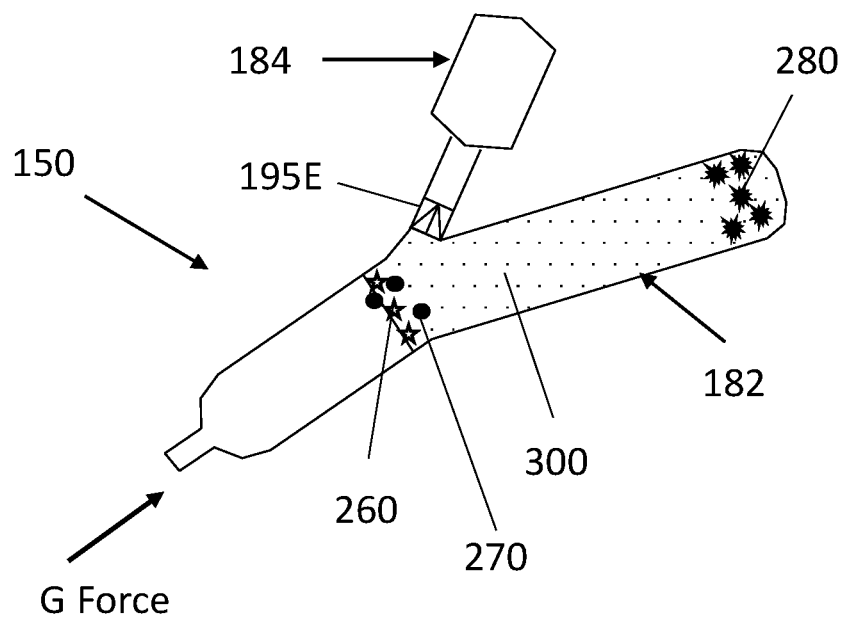
FIG. 9A—A schematic view demonstrating the secondary chamber with two wells.

Referring to FIG. 9A, the second chamber 150 containing density gradient fluid has a special geometry in its radially outer section. The radially outward end of the chamber 150 is split in two wells. The first well 182 extends radially outward and receives most of the density gradient fluid 300. A valve 195E controls the entrance to the second well 184.

Figure 9B:
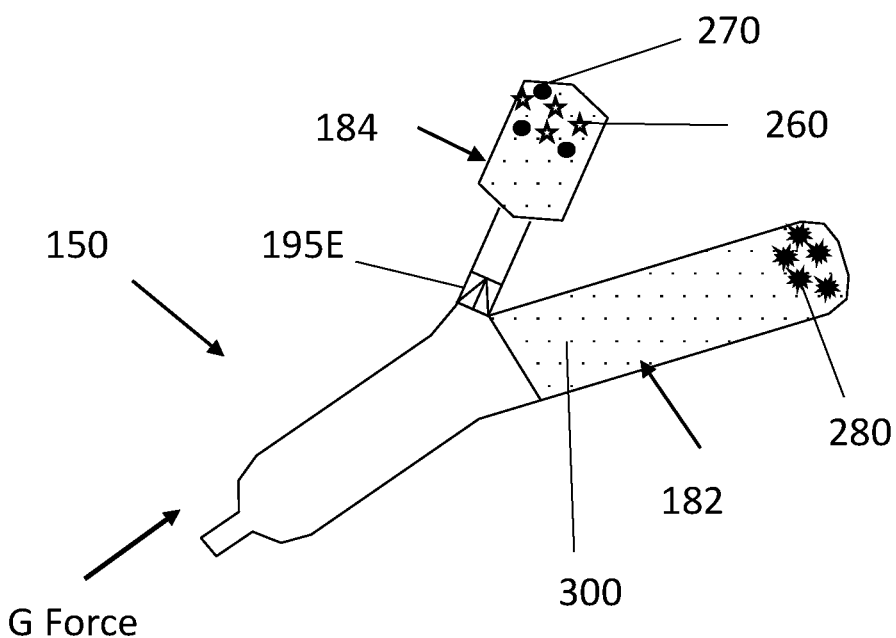

It is preferred that the gradient density fluid has a density (for example 1.075 g/ml) that is lighter than the granulocytes 280 but higher than the lymphocytes 270 and monocytes 260. By the effect of the centrifugal forces, the granulocytes 280 that have a density higher than the density gradient fluid are trapped at the outer bottom of the first well 182. The lighter density lymphocytes and monocytes are suspended on the surface of the gradient density fluid. Consequently, as shown in FIG. 9B, the valve 195E controlling the entrance to the second well 184 is opened and the gradient fluid along with the lymphocytes 270 and the monocytes 260 are rushed into the second well. Then the valve is closed. In case the monocytes 260 and the lymphocytes 270 are targeted, the second well 184 is equipped with ports (not shown) to drain or to recover all its contents by a syringe or a pipette. In another embodiment the second well forms a chamber that can be detached from the disc while all the harvested lymphocytes are trapped inside it. Therefore, the system can be used for applications that require to harvest T-cells that are mostly lymphocytes.

In case the granulocytes 280 are targeted, the first well 182 is equipped with ports (not shown) to drain or to recover all its contents by a syringe or a pipette. In another embodiment the first well forms a chamber that can be detached from the disc while all the harvested granulocytes (basophils, neutrophils, and eosinophils) are trapped inside it. Therefore, the system can be used for applications that require to harvest immune cells.

In another embodiment where maternal blood is processed, and the fetal NRBC cells are targeted. The buffy coat layer (platelets, monocytes, lymphocytes, granulocytes, and the fetal NBRC cells) is transferred to the secondary chamber inside the fluidic disc. This chamber contains specialty medium 305 that is prepared by mixing density gradient solution with a hypertonic solution to bring its osmotic pressure to a level that can increase the density of the NRBC to a level higher than the gradient solution. For example, Sodium Chloride solution or Sucrose solution could be used to alter the NRBC cells density.

It is important to mention that Polymorphprep contains dextran that could bind to NRBC cell membrane and eventually increase its density. Therefore, Polymorphprep is hypertonic to NRBC cells.

In other embodiment, gradient density fluid such as Percoll is mixed with dextran that could bind to NRBC cell membrane and eventually increase its density.

The valve 195D controlling the flow into the secondary chamber is closed. The rotor speed gradually drops to the vicinity of 100 rpm (or it stops) for a period of time 10 to 30 minutes enough for the osmotic pressure to draw fluid out of the NBRC cell in order to increase its density. This osmotic pressure and exposure time are enough for the fetal NBRC cells to have their density higher than the density of the gradient solution. The leukocytes are slow to respond to the hypertonic solution during this duration and their density wouldn't change. The leukocyte would react to a long exposure time to the hypertonic solution and their density could increase. Therefore, the hypertonic exposure timing must be closely monitored. Since the NRBC cells density is controllably changeable from that of the leukocytes, they can be separated from the leukocytes by density gradient centrifugation. The centrifuge rotor speed is increased in order to ensure the sedimentation of the dens NRBC at the outer edge of the secondary chamber.

Figure 10:
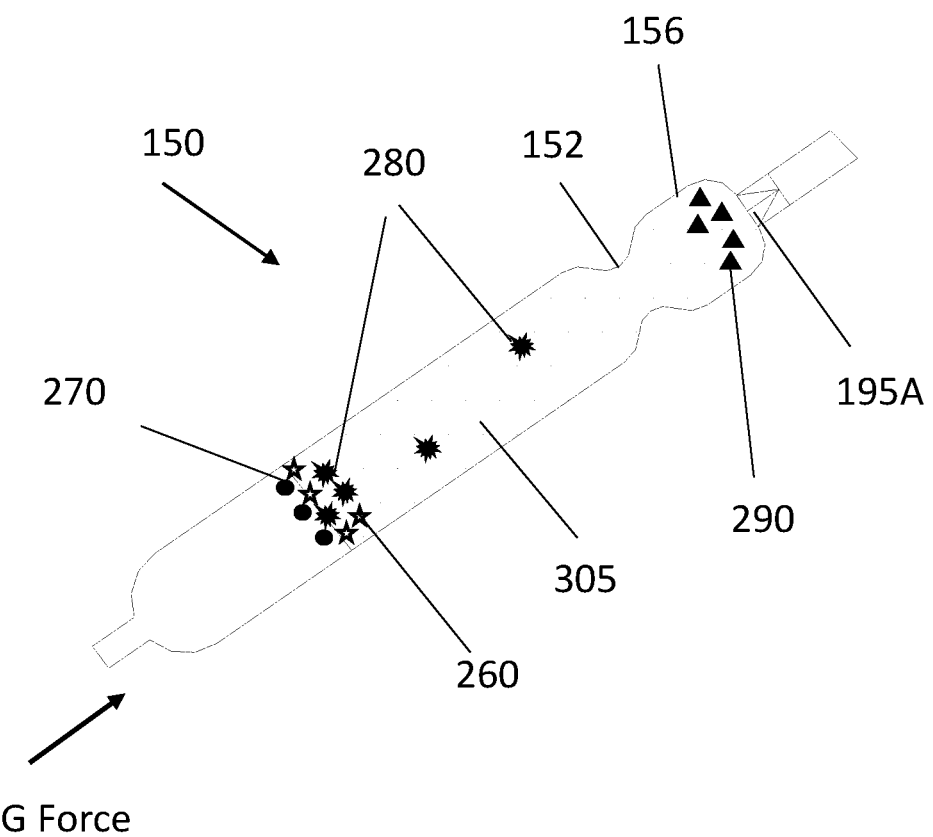
FIG. 10—A schematic view demonstrating the separation of altered density cells inside the secondary chamber.

Referring to FIG. 10, the secondary chamber contain a medium 305 that is a mixture of Percoll (density gradient solution) with a hypertonic solution (NaCl) that has an osmotic pressure ranging (380 mOsm to 450 mOsm); with density ranging (1.085 g/ml to 1.095 g/ml). Only the cells with a density higher than the medium solution density, precipitate at the bottom of the exterior cavity 156. The NRBC cells 290 that are subjected to osmotic pressure for a period of time that increases its density beyond the density of the medium 305. Few granulocytes 290 that have the same density of the medium are suspended in the medium fluid. Most of the granulocytes 290 and the entire colonies of the monocytes 260 and lymphocytes 270 are floating on the surface of the medium closer to the axis of rotation. In case the platelets are transferred to the secondary chamber with the rest of the buffy coat layer, they get to float on the surface of the medium closer to the axis of rotation as well.

Figure 11:
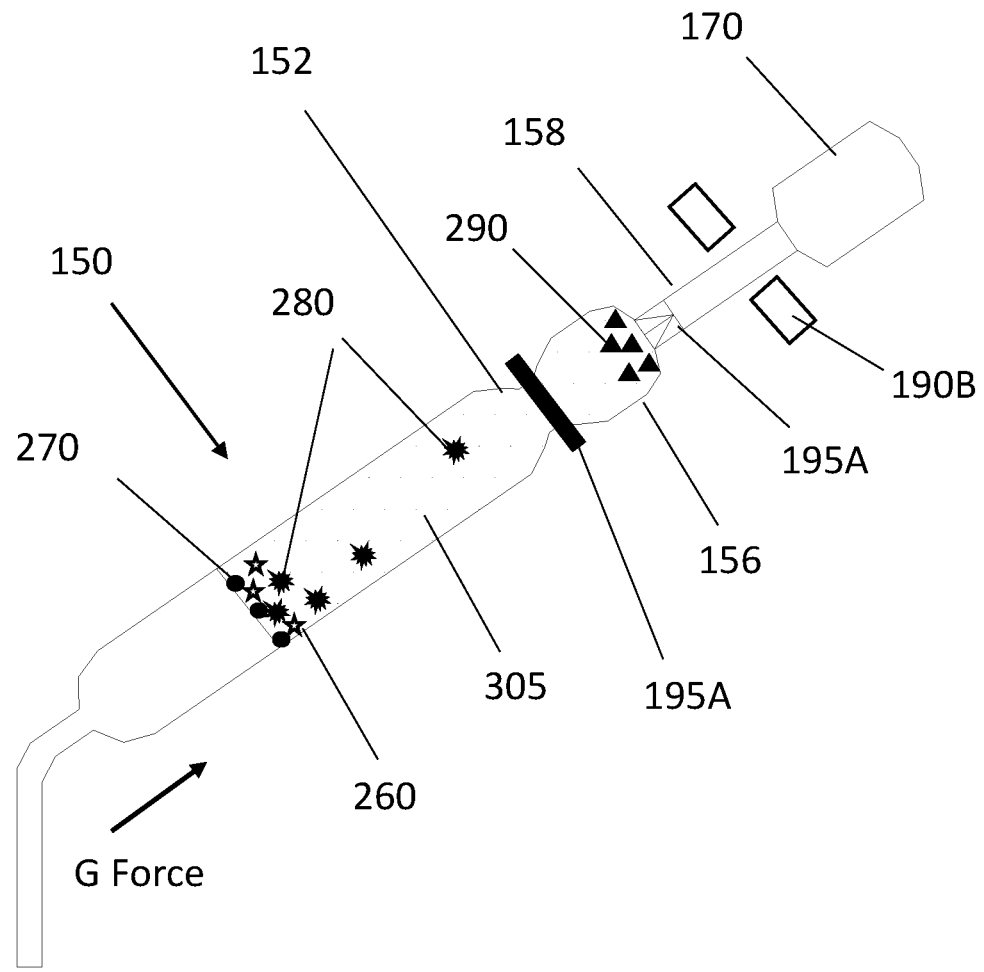
FIG. 11—A schematic view demonstrating the isolation of altered density NRBC inside the secondary chamber.

Referring to FIG. 11, the gorge occlusion valve 195F is activated to seal the exterior cavity 156 that contains a concentrated colony of NRBC 290. The exterior cavity 156 is equipped with ports (not shown) to drain or to recover all its contents by a syringe or a pipette.

In a preferred embodiment, the disc 100 encompasses a detachable chamber 170 positioned radially outward with respect to the exterior cavity 156 as shown in FIG. 11. This detachable chamber is designed to receive cells including the NRBC from the exterior cavity by centrifugal forces via a fluidic channel 158. Valve 195A controls the fluid flow through the channel 158 connecting the exterior cavity 156 to the detachable chamber 170. The rotor spins at about 100 rpm and the valve 195A is opened for a period of time enough to ensure the complete transfer of the NRBC 290 to the detachable chamber 170. Then the valve is closed.

In another embodiment, an optic sensor 190B is positioned on the fluidic channel 158 to determine the completion of the fluid transfer process between the exterior cavity 156 and the detachable chamber 170.

In another embodiment, the fluidic channels 158 of each processing station are all set to converge to one common chamber that preferably located in the central part of the disc 100. It is preferable that this common chamber could have special ports to drain the stored fluid; or to extract the stored fluid by pipetting or by a syringe. It is also preferable that this common chamber could be detachable from the disc. In this arrangement all the harvested cells from all the processing stations are accumulated in one chamber.

At the end of the procedure, the centrifuge is stopped and the fluidic disc is removed from the rotor. The detachable chamber is disconnected from the disc and sealed with a cap. The harvested NRBC colony is safely preserved inside the chamber to be transported to the appropriate laboratory for analysis.

The fluid inside detachable NBRC chamber is drained out. Staining such as Wright and Giemsa stains or May-Grünwald-Giemsa is used to stain the nucleated cells and to identify the fetal NBRC cells under the microscope.

The standard (Non-nucleated) red blood cells are not affected by Giesma staining because these cells don't have nucleus. Therefore, a presence of a moderate number of these cells in the final product should not affect the search for the NRBC cells under the microscope.

There is a distinguished difference in the morphology of the NRBC and the granulocytes (basophils, neutrophils, and eosinophils). The NRBC has a one large sphere shaped nucleus while the granulocytes have nucleus formed of multiple grains connected together.

The NRBC fetal cells are detected and separated from the harvested colony of the nucleated cells. DNA analysis such as Polymerase Chain Reaction (PCR) are conducted on the isolated NRBC to determine fetus DNA and chromosome information.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of all references, issued patents, and published patent applications cited throughout this application are hereby incorporated by reference. The appropriate components, processes, and methods of those patents, applications and other documents may be selected for the present invention and embodiments thereof.

The invention claimed is:

1. A method for isolating and retrieving nucleated cells in blood by automatically processing whole blood or bone marrow using a system comprising a disc integrated with a spinning rotor having an axis of rotation, the disc is fitted to receive blood or bone marrow before or after being mounted to a centrifuge rotor to start automated processing operation independent of human interference, the disc encompasses at least two processing stations that are equidistantly separated and are symmetrically related with respect to the axis of rotation, the disc incorporates a channel on its periphery that encircles all the processing stations and providing a fluidic communication between said processing stations, each processing station comprises at least one radially extended chamber with its outer edge merging with the peripheral encircling channel, whereas the inner edge of said chamber merges into a radial channel that branches at its end into channels connecting secondary chambers, at least one secondary chamber on each processing station contains one or more fluid wherein each fluid having a specified density ranging between 1.0 gram/ml and 1.12 gram/ml, the volume defined by the radially extended chambers on all the processing stations and the peripheral encircling channel is set to receive blood or bone marrow for processing, whereas fluids inside said volume can be compressed to generate fluid flow within the processing stations, the disc is fitted to engage with the centrifuge rotor allowing devices and sensors located on the rotor to control fluids, nucleated cells, and blood components movements within each processing station on the disc for the execution of first stage separation and second stage separation as directed by a software protocol, wherein all processing steps are synchronized on all the processing stations on the disc, the first stage separation processes whole blood or bone marrow using centrifugation forces to separate the blood or the bone marrow components in distinctive density layers, transfer the plasma layer into the first secondary chamber and maintain a layer of nucleated cell mixture in another secondary chamber on each blood processing station, the second stage separation process in each blood processing station comprises the transfer of the separated layer of the nucleated cell mixture resulted from the first stage into a secondary chamber containing fluid with a specified density that is relatively less than the density of the targeted cells, wherein the targeted nucleated cells are sedimented by centrifugal forces at the outer most section of the secondary chamber with respect to the axis of rotation, or the density of the fluid is relatively more than the density of the targeted cells, wherein the targeted nucleated cells are accumulated by centrifugal forces at the fluid surface closer to the axis of rotation, wherein the targeted nucleated cells are selected from the group consisting of mononuclear monocytes, lymphocytes, granulocytes, neutrophils, basophils, eosinophils, stem cells, cancer cells, immune cells, and nucleated red blood cells.

2. A method for isolating and retrieving nucleated red blood cells by automatically processing maternal blood using a system comprising a disc integrated with a spinning rotor having an axis of rotation, whereas maternal blood is defined as blood obtained from a pregnant woman, the disc is fitted to receive blood before or after being mounted to a centrifuge rotor to start automated processing operation independent of human interference, the disc encompasses at least two processing stations that are equidistantly separated and are symmetrically related with respect to the axis of rotation, the disc incorporates a channel on its periphery that encircles all the processing stations and providing a fluidic communication between said processing stations, each processing station comprises at least one radially extended chamber with its outer edge merging with the peripheral encircling channel, whereas the inner edge of said chamber merges into a radial channel that branches at its end into channels connecting secondary chambers, at least one secondary chamber on each processing station contains one or more fluid wherein each fluid having a specified density, the volume defined by the radially extended chambers on all the processing stations and the peripheral encircling channel is set to receive maternal blood for processing, whereas fluids inside said volume can be compressed to generate fluid flow within the processing stations, the disc is fitted to engage with the centrifuge rotor allowing devices and sensors located on the rotor to control fluids, cells, and blood components movements within each processing station on the disc for the execution of first stage separation and second stage separation as directed by a software protocol, wherein all processing steps are synchronized on all the processing stations on the disc, the first stage separation processes maternal blood using centrifugation forces to separate the blood components in distinctive density layers, transfer the plasma layer into the first secondary chamber, and maintain a layer of nucleated blood cell mixture in each blood processing station, the second stage separation process in each blood processing station comprises the transfer of the separated layer of the nucleated blood cell mixture resulted from the first stage into a secondary chamber containing fluid with a specified density ranging between 1.075 gram/ml and 1.12 gram/ml that ensures the sedimentation of the nucleated red blood cell by centrifugal forces at the outer most section of the secondary chamber with respect to the axis of rotation to be harvested from the disc at the end of the procedure.

3. The method as defined in claim 1 or 2, wherein the disc is fitted with pumping means that engages with one or more actuating device on the centrifuge rotor to generate a recirculation flow of separated plasma stored in a secondary chamber back into the concentrated red blood cell layer amassed in the radially extended chamber or in the peripheral encircling channel, wherein generated plasma flow releases trapped nucleated cells from the concentrated red blood cell layer.

4. The method as defined in claim 1, wherein the secondary chamber containing density gradient fluid has its outer end split in two wells, one well extends radially outward to receive the cells that have a density higher than the density gradient fluid, the second well is gated and it extends outwardly in an oblique direction with respect to the first well, whereas after the sedimentation of the cells having density higher than the density of the density gradient fluid in the first well, the gated well is opened and the cells having density less than or equal to the density of the density gradient fluid are driven into the second well and are stored therein.

5. The method as defined in claim 1, wherein the density gradient fluids used to isolate blood cells of specified density, are selected from a group consisting of Percoll solution, Ficoll solution, Polymorphprep solution, sucrose, Nycodenz, and OPTIPrep.

6. The method as defined in claim 1, wherein the density gradient fluid having osmotic pressure ranging between 300 mOsm and 600 mOsm, used to soak nucleated cells for a period of time enough to change its density to a predetermined level.

7. The method as defined in claim 1 or 2, wherein the targeted nucleated cells accumulated inside a specified secondary chamber on each processing station can be harvested from the disc at the end of the procedure by a syringe or a pipet suction from a port on the disc, or by having the targeted cells stored inside a container connected to said chamber and it is detachable from the disc.

8. The method as defined in claim 1 or 2, wherein the disc is equipped with a chamber containing hypertonic or hypotonic solution that is set to receive the nucleated cells for a period of time enough to change its density to a predetermined level before their transfer to the secondary chamber containing density gradient fluid.

9. The method as defined in claim 1 or 2, wherein the medium of the density gradient fluid used in the secondary chamber is composed of at least of two chunks of density fluids having different densities one stacked on the top of the other.

10. The method as defined in claim 1 or 2, wherein the density of the density gradient fluid ranging between 1.085 gram/ml and 1.095 gram/ml.

11. The method as defined in claim 1 or 2, wherein the density gradient fluid having osmotic pressure ranging between 380 mOsm and 450 mOsm.

12. The method as defined in claim 2, wherein the density gradient fluid is Percoll solution or Ficoll solution.

13. The method as defined in claim 1 or 2, wherein the density gradient fluid is a mixture of Percoll solution and NaCl solution that brings its osmotic pressure to a level ranging between 380 mOsm and 450 mOsm.

14. The method as defined in claim 1 or 2, wherein the density gradient fluid Polymorphprep solution with osmotic pressure ranging between 420 mOsm and 500 mOsm, and density ranging between 1.108 gram/ml and 1.118 gram/ml.

15. The methods as defined in claim 1 or 2, wherein the execution of the first stage separation includes;
the high-density components inside the peripheral encircling channel are evenly pushed inside all the radially extended chambers on all the processing stations forcing low-density plasma to flow out of said chambers and into the first secondary chamber on each processing station, and
controlled compressing mechanisms are activated on the radially extended chambers on all the processing stations to slowly express the remining plasma out of said chambers and into the first secondary chamber on each processing station on the disc, and
sensors detecting fluid density on the radial channels of the radially extended chambers on all the processing stations influence flow redirection to drive the exiting nucleated cells and platelets mixture into a specified secondary chamber on each processing station on the disc.

16. A method for isolating and retrieving nucleated cells in blood by automatically processing whole blood or bone marrow using a system comprising a disc integrated with a spinning rotor having an axis of rotation,
the disc is fitted to receive blood or bone marrow before or after being mounted to a centrifuge rotor to start automated processing operation independent of human interference,
the disc incorporates at least two processing stations that are equidistantly separated and are symmetrically related With respect to the axis of rotation
the disc incorporates a channel on its periphery that encircles all the processing stations and providing a fluidic communication between said processing stations,
each processing station comprises at least one radially extended chamber with its outer edge merging with the peripheral encircling channel, whereas the inner edge of said chamber merges into a radial channel that branches at its end into channels connecting secondary chambers,
the volume defined by the radially extended chambers on all the processing stations and the peripheral encircling channel is set to receive blood or bone marrow for processing, whereas fluids inside said volume can be compressed to generate fluid flow within the processing stations,
the disc is fitted to engage with the centrifuge rotor allowing devices and sensors located on the rotor to control the movements of bone marrow and blood components movements between the peripheral channel and the processing stations and to control the movements of fluids, nucleated cells, bone marrow components, and blood components within each processing station on the disc, wherein all processing steps are synchronized on all the processing stations on the disc,
centrifugation forces on the spinning rotor separate the blood or the bone marrow components in distinctive density layers,
wherein the execution steps of said method include;
the high-density components inside the peripheral channel are evenly pushed inside all the radially extended chambers on all the processing stations forcing low-density plasma to flow out of said chambers and into the first secondary chamber on each processing station, and
controlled compressing mechanisms are activated on the radially extended chambers on all the processing stations to slowly express the remining plasma out of said chambers and into the first secondary chamber on each processing station on the disc, and
sensors detecting fluid density in the radial channels of the radially extended chambers on all the processing stations influence flow redirection to drive the exiting nucleated cells and platelets mixture into a specified secondary chamber on each processing station on the disc, and
nucleated cells and platelets mixture are accumulated at the outer section of said specified secondary chamber on each processing station and stored radially beyond a gate with respect to the axis of rotation, to be harvested by a syringe or a pipet from a port on the disc, or by having the targeted cells mixtures stored inside a container connected to said chamber and it is detachable from the disc,
wherein the nucleated cells are selected from the group consisting of mononuclear monocytes, lymphocytes, granulocytes, neutrophils, basophils, eosinophils, stem cells, cancer cells, immune cells, and nucleated red blood cells.

17. The method as defined in claim 16, wherein the disc and rotor are fitted jointly with pumping means to affect a recirculation flow of separated plasma stored in a secondary chamber back into the concentrated red blood cell layer amassed in the radially extended chamber or in the circular channel, whereas said recirculating flow frees trapped nucleated blood cells from the amassed red blood cells layer.

18. The method as defined in claim 16, wherein the secondary chamber on each processing station that receives nucleated blood cells and platelets mixture or bone marrow cells and platelets mixture, contains one or more fluid or density gradient fluid used to isolate blood cells of specified density, wherein each fluid having a specified density ranging between 1.0 gram/ml and 1.12 gram/ml, wherein the density gradient fluids are selected from a group consisting of Percoll solution, Ficoll solution, Polymorphprep solution, sucrose, Nycodenz, and OPTIPrep.

19. The method as defined in claim 16, wherein the secondary chamber on each processing station that receives nucleated blood cells and platelets mixture or bone marrow cells and platelets mixture, contains one or more fluid or density gradient fluid having osmotic pressure ranging between 300 mOsm and 600 mOsm, used to influence the densities of the blood cells.

20. The method as defined in claim 1 or 2, wherein the whole procedure for isolating and retrieving nucleated cells by automatically processing whole blood, maternal blood, or bone marrow is conducted continuously inside the disc and centrifuge system for the execution of first stage separation and second stage separation as directed by a software protocol without human interference, whereas the targeted cells are manually harvested from the disc post the processing operation.

* * * * *